US006174880B1

(12) United States Patent
Bernstein

(10) Patent No.: US 6,174,880 B1
(45) Date of Patent: Jan. 16, 2001

(54) METHOD FOR TREATMENT OF PAINFUL FIBROMUSCULAR DISORDER

(75) Inventor: Joel E. Bernstein, Deerfield, IL (US)

(73) Assignee: Winston Laboratories, Inc., Vernon Hills, IL (US)

(*) Notice: Under 35 U.S.C. 154(b), the term of this patent shall be extended for 0 days.

(21) Appl. No.: 09/203,060

(22) Filed: Dec. 1, 1998

(51) Int. Cl.$^7$ .................................................. A61K 31/55
(52) U.S. Cl. ..................... 514/217; 514/450; 514/643; 514/654
(58) Field of Search .................................. 514/217, 450, 514/643, 654

(56) References Cited

U.S. PATENT DOCUMENTS 4,395,420   7/1983   Bernstein .

FOREIGN PATENT DOCUMENTS

WO 9710815   3/1997   (WO) .

OTHER PUBLICATIONS

*Textbook of Pain,* Wall, Patrick D. et al., Third Edition, (1994), pp. 476–480.
*Textbook of Rheumatology,* Kelley, William N., M.D. et al., (1989), pp. 541–553.
Treatment of Painful Diabetic Neuropathy With Topical Capsaicin, *Arch. Intern. Med.,* vol. 151, Nov. 1991, pp. 2225–2229.
"A Randomized Vehicle–Controlled Trial of Topical Capsaicin in the Treatment of Postherpic Neuralgia," Watson et al., *Clinical Therapeutics,* vol. 15, No. 3, 1992, pp. 510–526.
"Treatment of Arthritis with Topical Capsaicin: A Double–Blind Trial," Deal et al., *Clinical Therapeutics,* vol. 13, No. 3, 1991, pp. 383–395.

*Primary Examiner*—Rebecca Cook
(74) *Attorney, Agent, or Firm*—Jones, Day, Reavis & Pogue

(57) ABSTRACT

A method for treating painful fibromuscular disorders comprising topical application to the skin of a therapeutically effective amount of a tricyclic antidepressant compound in a pharmaceutically acceptable vehicle.

5 Claims, No Drawings

METHOD FOR TREATMENT OF PAINFUL FIBROMUSCULAR DISORDER

BACKGROUND OF THE INVENTION

Painful fibromuscular disorders are common causes of pain and disability. In particular, fibrositis (also known as fibromyalgia) is a type of fibromuscular disorder that is a frequent cause of debilitating pain arising within muscles or muscle-tendon and tendon-bone junctions. Fibrositis is seen more frequently in women and is characterized by four constant features: pain, stiffness, fatigue and non-restorative sleep. In contrast with most rheumatic disorders, fibrositis rarely is responsive to corticosteroids and non-steroidal anti-inflammatory drugs. The only area in which medications are currently of proven value is in management of the associated sleep disorder.

I have discovered that tricyclic anti-depressants, usually prescribed orally for relief of mental depression or applied topically to the skin to relieve itching in dermatitis as described in my prior U.S. Pat. No. 4,395,420, are surprisingly effective at relieving or moderating the pain, stiffless, fatigue and sleep disorder associated with fibromuscular disorders such as fibrositis when applied topically. These compounds include the pharmaceutically acceptable salts of the tricyclics. The term pharmaceutically acceptable salts, as used herein, refers to the physiologically acceptable acid addition salts such as the hydrochloride, hydrobromide, hydroiodide, acetate, valerate, oleate, etc. Doxepin, amitriptyline and imipramine respectively are the tertiary amine derivatives of dibenzoxepin, dibenzoycloheptadiene and dibenzazepine wherein the nitrogen atom is connected to the ring structure by a three carbon aliphatic chain and the tertiary amine has two carbon atoms attached thereto in addition to the aliphatic chain.

The present invention relates to a method for topically treating fibromuscular disorders such as fibrositis. The principal object of the present invention is to apply topically divided doses of tricyclic anti-depressant compounds traditionally employed systematically for treatment of mental depression to relieve pain, stiffness, fatigue and sleep disorders characteristic of fibrositis. It is speculated that alleviation of the associated sleep disorder may arise either from relief of the pain and stiffness that prevented restful sleep, and/or from the sedative effect that these compounds are known to provide when administered systemically.

This and other objects of the present invention may be more readily understood when considered in conjunction with the following detailed description and examples.

DETAILED DESCRIPTION OF THE PREFERRED EMBODIMENTS

I investigated the possible therapeutic effects of topically applied formulations of tricyclic anti-depressant compounds in fibrositis by having patients suffering from fibrositis apply doxepin hydrochloride to localized areas of pain and/or stiffness. Patients noted not orgy relief of pain and stiffness as a consequent of such method of treatment, but also reported less fatigue and difficulty sleeping.

In the practice of the invention, concentrations of salts of doxepin, amitriptyline and imipramine varying from about 1% by weight to about 10% by weight will be incorporated into creams, ointments, lotions and solutions and applied to patients suffering from fibromuscular disorders in divided doses for the relief of the pain, stiffness, and/or fatigue associated with such disorders. The preferred amount of active ingredients will be from about 1% to about 5% by weight of the carrier.

The following examples further illustrate the invention. In these examples, all percentages are by weight of the carrier.

EXAMPLE 1

A cream containing 5% of the commonly administered tricyclic antidepressant compound doxepin hydrochloride was topically applied to the lower neck, shoulders and back of a 53 year old female with pain and stiffness in these areas, as well as accompanying non-restorative sleep and fatigue. Within several days of twice daily application of this cream the patient was experiencing substantially less pain and stiffness in the neck, shoulders and back and was better rested upon awakening in the morning and less fatigued during the day.

EXAMPLE 2

A cream containing 1% doxepin hydrochloride was applied once daily for two weeks to the lower legs of a 55 year old male with pain and stiffness in the medial knee and upper Achilles tendon area of the feet. The patient experienced considerably less pain and stiffness in his legs and feet, was able to obtain more restful sleep at night, and was less fatigued during the day.

EXAMPLE 3

A 54 year old woman with diffuse pain and stiffness unresponsive to non-steroidal anti-inflammatory drugs (NSAIDS) applied a 5% cream containing doxepin hydrochloride several times daily to her neck, shoulders, and arms She related that she received almost immediate relief from pain and stiffness following each application of the doxepin cream and felt she was able to function considerably better during the day than when on NSAIDS.

It will be apparent to those skilled in the art that only the preferred embodiments have been described by way of example and that there are various modifications that fall within the scope of this invention.

What is claimed is:

1. A method for treatment of one or more symptoms of fibromyalgia selected from the group consisting of localized pain and stiffness comprising applying topically to a site of said localized pain or stiffness a therapeutically effective amount of a tricyclic anti-depressant compound in a pharmaceutically acceptable vehicle.

2. The method of claim 1 wherein said tricyclic anti-depressant is present in the vehicle in the range of 1% to 10% by weight of the vehicle.

3. The method of claim 1 wherein said tricyclic anti-depressant compound is selected from the group consisting of doxepin, amitriptyline, imipramine or a physiologically acceptable acid addition salt thereof.

4. The method of claim 1 wherein said physiologically acceptable acid addition salt is selected from the group consisting of the hydrochloride, hydrobromide, hydroiodide, acetate, valerate and oleate.

5. The method of claim 1 wherein said pharmaceutically acceptable vehicle is selected from the group consisting of creams, ointments, lotions, and solutions.

* * * * *